(12) United States Patent
Samuelsson

(10) Patent No.: US 6,824,537 B1
(45) Date of Patent: Nov. 30, 2004

(54) ABSORBENT ARTICLE WITH BELLOW PLEATS ALLOWING TRANSVERSAL EXPANSION

(75) Inventor: Ann Samuelsson, Lindome (SE)

(73) Assignee: SCA Hygiene Products AB, Gothenburg (SE)

( * ) Notice: Subject to any disclaimer, the term of this patent is extended or adjusted under 35 U.S.C. 154(b) by 176 days.

(21) Appl. No.: 10/111,757
(22) PCT Filed: Oct. 10, 2000
(86) PCT No.: PCT/SE00/01956
§ 371 (c)(1), (2), (4) Date: Aug. 12, 2002
(87) PCT Pub. No.: WO01/32118
PCT Pub. Date: May 10, 2001

(30) Foreign Application Priority Data
Nov. 3, 1999 (SE) .............................................. 9903984

(51) Int. Cl.[7] .............................................. A61F 13/15
(52) U.S. Cl. .......................... 604/385.201; 604/385.01; 604/385.17; 604/385.16
(58) Field of Search ..................... 604/385.201, 385.22, 604/385.28, 385.01, 385.16, 385.17, 385.19

(56) References Cited

U.S. PATENT DOCUMENTS 3,865,111 A * 2/1975 Brooks ........................ 604/378
4,014,338 A * 3/1977 Schaar ........................ 604/389
4,883,481 A * 11/1989 Blanchard ............... 604/385.11
5,662,636 A * 9/1997 Benjamin et al. ....... 604/385.28
5,824,004 A   10/1998 Osborn, III et al.
6,149,638 A * 11/2000 Vogt et al. ............. 604/385.01
6,248,098 B1 * 6/2001 Sayama ................. 604/385.28

FOREIGN PATENT DOCUMENTS

EP    0 405 403 A2    1/1991
WO    98/15246        4/1998

* cited by examiner

Primary Examiner—John J. Calvert
Assistant Examiner—Jacqueline F Stephens
(74) Attorney, Agent, or Firm—Burns, Doane, Swecker & Mathis, L.L.P.

(57) ABSTRACT

An absorbent article is provided in the form of a sanitary napkin, a panty liner or an incontinence protector, having an elongated body that includes an expansion element for permitting the body to expand in a direction generally transversely to the elongated body. The elongated body is flat and has a liquid-permeable sheet that is intended to face toward the wearer's body, a liquid-impermeable sheet that is intended to face towards a wearer's garment, and an absorbent layer disposed between the liquid-permeable sheet and the liquid-impermeable sheet. The liquid-impermeable sheet may include a fastener for enabling the absorbent article to be releasably fastened to the garment. The expansion element may include a pleat which extends only partially along the elongated body.

10 Claims, 2 Drawing Sheets

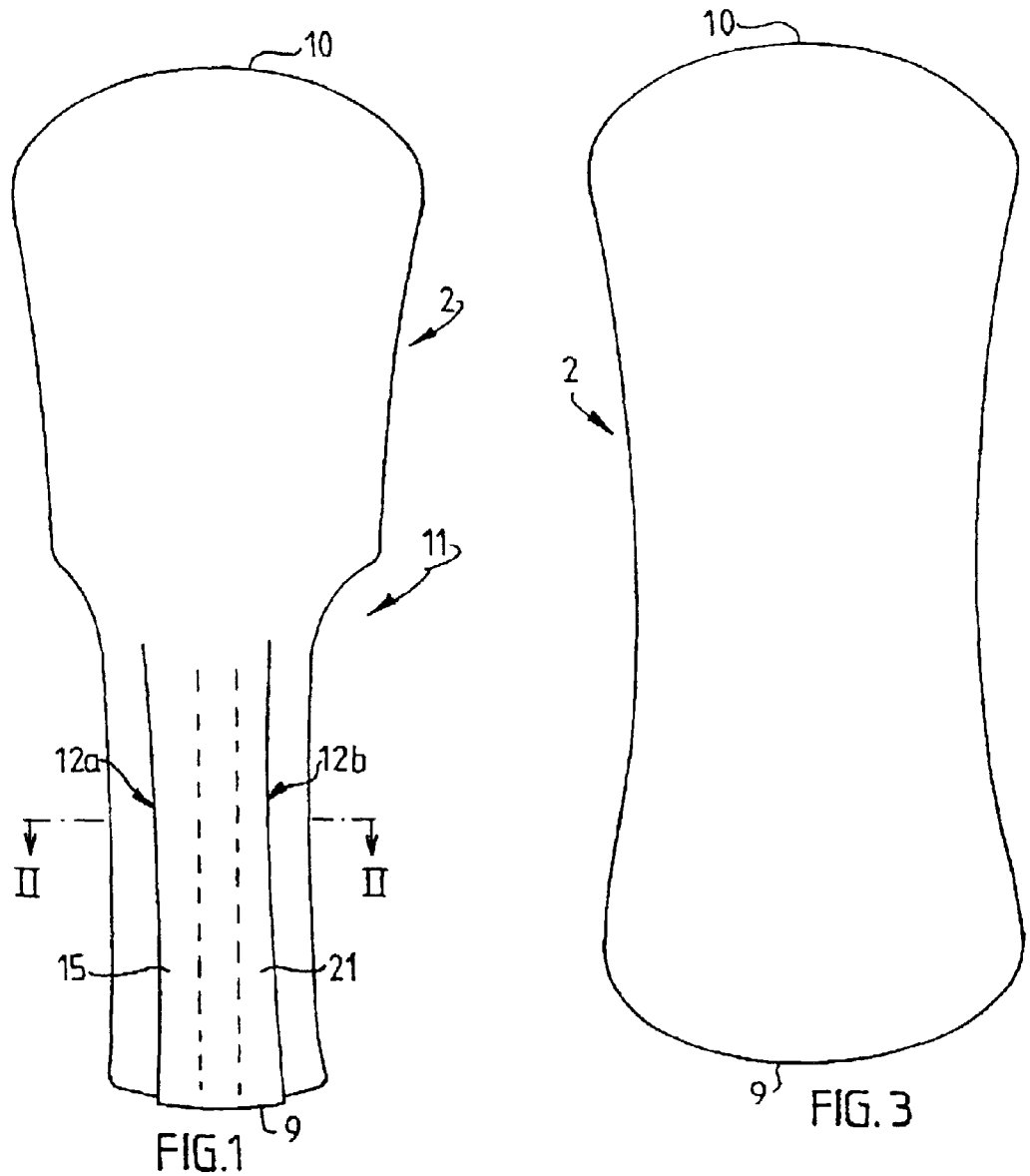
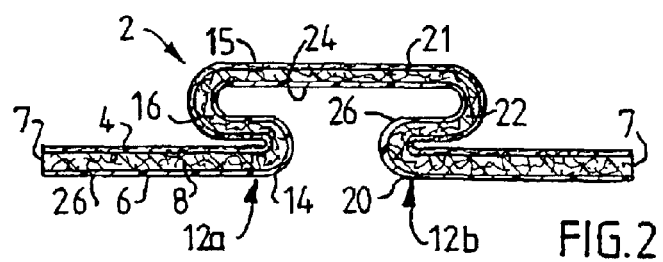

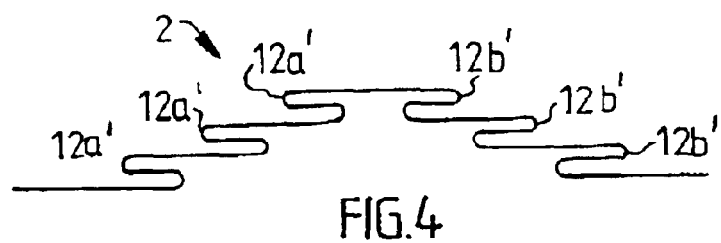
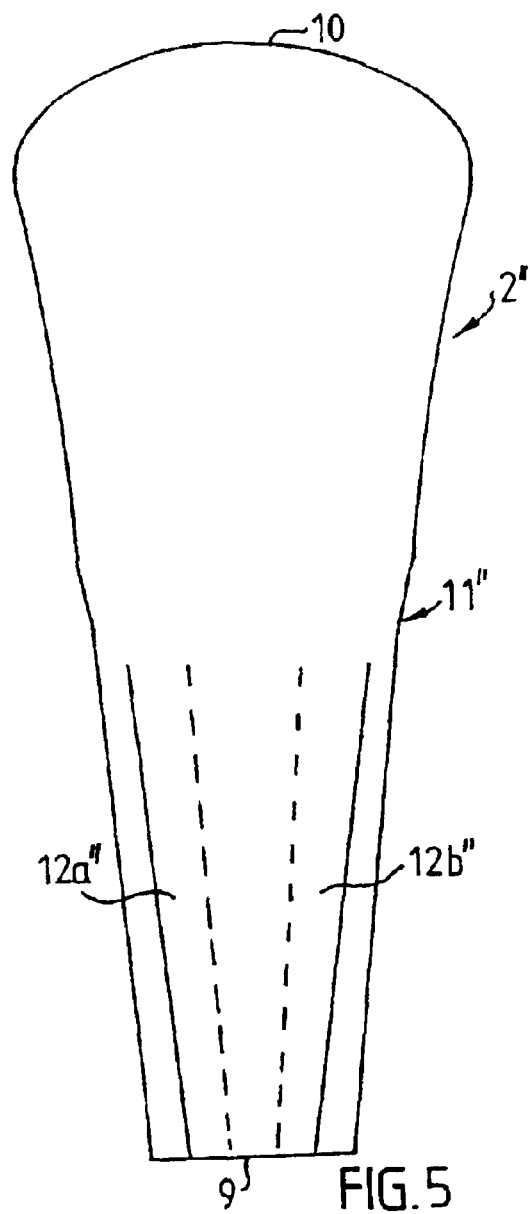

ABSORBENT ARTICLE WITH BELLOW PLEATS ALLOWING TRANSVERSAL EXPANSION

TECHNICAL FIELD

The present invention relates to an absorbent article in the form of a sanitary napkin, a panty liner or an incontinence protector, comprising an elongated body that includes means for permitting the body to expand in a direction essentially transversely to said elongated body, wherein the elongated body is flat and has a liquid-permeable sheet or layer which is intended to face towards the crotch of the wearer in use, a liquid-impermeable sheet which is intended to face towards a garment, such as a pair of panties worn by the user, and an absorbent layer disposed between the liquid-permeable sheet and the liquid-impermeable sheet, wherein said liquid-impermeable sheet is provided at least partially with fastener devices that enable the article to be connected releasably to said garment.

DESCRIPTION OF THE BACKGROUND ART

An article of this kind is known from EP-A-0 405 403 which teaches a panty liner that includes a single pleat or fold that extends along the full length of the elongated body, so as to enable the panty liner to expand in a direction transversely to the elongated body and therewith fit garments of different sizes. The pleat or fold, however, extends towards the wearer's body and can therefore cause discomfort to the wearer. For this reason, the pleated part of the panty liner may have only a small vertical extension, and it is only possible to adapt the known panty liner to a very limited range of garment sizes. Moreover, the known pleat, or fold, has a stiffening effect against bending of the article about transversal axes in the plane of the article, which limits the ability of the known panty liner to adapt to the wearer's body shape in use.

Accordingly, the object of the present invention is to provide a discrete panty liner that can be adapted to many different garment sizes but which, nevertheless, can be worn comfortably and which can readily adapt to the body shape of the wearer.

SUMMARY OF THE INVENTION

This object has been achieved with an absorbent article of the kind defined in the introductory paragraph and characterised in that said expansion means includes at least one bellows-like pleat that extends only partially along the elongated body and that includes two leg parts disposed in plane parallel with the plane of the article, and an inwardly folded intermediate part that extends between said leg parts and joins said leg parts together. This results in an absorbent article that covers the whole of the garment area that faces towards the urethra and vagina of the wearer, but which is narrow in the region of the article that is placed against the pelvis and the anus of the wearer. Thus, in a known-expanded state the article is adapted to suit string panties but can be expanded to fit panties that have a traditional crotch. The total absorption capacity of the article is the same, regardless of whether it is folded or not. Because the pleat is a bellows-like pleat, the inwardly folded parts of the article will be directed essentially parallel with the plane of the article, meaning that the article has generally planar surfaces and that the stiffening effect afforded by the pleat essentially influences only bending of the article about axes that extend perpendicular to the plane of the article and will not therefore limit its ability to adapt to the body shape of the wearer other than the limitation incurred by the greater thickness of the material in the inwardly folded parts of the article, which, of course, slightly increases the bending resistance. Because the pleat or pleats is layered solely located in the rear part of the article when worn, the pleat/pleats will have no negative affect on the ability of the front part of the article to adapt to the body shape of the wearer.

The article will preferably include a pair of mirror-imaged bellows-like pleats on respective sides of the longitudinal symmetry axis of the article, said pleats having a cross-section in the general shape of a Z and a mirror-imaged Z respectively, wherewith the leg parts of the Z-shaped bellow-like pleats in the pair of pleats, which lie in the same plane, face towards each other. As a result of this configuration of the pleats in the rear part of the article, the article will tend to form a basin-like shape in the front part of the region nearest the beginning of the pleats, when the article is worn. Furthermore, this pleat configuration facilitates symmetric expansion of the rear part of the article. Such symmetrical expansion is important in ensuring that the front part of the article will not lie crookedly in use.

The expansion means will suitably include several pairs of bellows-like pleats. This provides the possibility of extending the panty liner with successive pairs of pleats, so as to fit garments of all particular sizes.

The inwardly folded intermediate parts of the pleats are conveniently releasably joined to the mutually facing leg parts. This can be achieved by applying a binder to the liquid-permeable sheet of the intermediate parts or the leg parts.

The elongated body will conveniently include a first and a second end and a central region therebetween, wherewith the pleats extend to the central region, from said first end towards said second end.

The pleats preferably extend parallel with one another. Alternatively, the pleats may extend in a divergent relationship with one another, therewith imparting different shapes to the rear part of the article.

The aforementioned fastener means will suitably be a binding agent. The binding agent may, in particular, comprise a pressure sensitive hotmelt glue.

BRIEF DESCRIPTION OF THE DRAWINGS

The present invention will now be described in more detail with reference to exemplifing embodiments thereof and also with reference to the accompanying drawings, in which FIG. 1 is a plan view of a folded panty liner according to a first embodiment of the invention;

FIG. 2 is a cross-sectional view taken on the line II—II in FIG. 1;

FIG. 3 is a plan view illustrating the panty liner of FIG. 1 in an unfolded state;

FIG. 4 illustrates schematically a second embodiment of a panty liner in a similar cross-sectional view to that of FIG. 2; and FIG. 5 illustrates a folded panty liner according to a third embodiment of the invention.

DESCRIPTION OF EMBODIMENTS

FIGS. 1–3 illustrate a panty liner 2 comprising a liquid-permeable sheet 4 which is intended to face towards the skin of a wearer's crotch, and a liquid-impermeable sheet 6 which is intended to face towards a wearer's garment, such as the wearer's panty, in use. The sheets 4 and 6 are joined together with a peripheral join 7. An absorbent layer 8 is disposed between the liquid-permeable sheet 4 and the liquid-impermeable sheet 6.

The liquid-permeable sheet 4 is preferably comprised of nonwoven material, although it may alternatively comprise perforated plastic film, a net of plastic or textile material, or a laminate of, e.g., a perforated plastic sheet and a nonwoven sheet. The plastic is preferably a thermoplastic material, e.g. polyethylene (PE). The nonwoven material is preferably comprised of natural fibres, such as cellulose or cotton, although it may, alternatively, comprise synthetic fibres, such as polyethylene (PE), polypropylene (PP), polyurethane (PU), a polyester, nylon or regenerated cellulose. All materials that are used for top sheets in absorbent articles, such as sanitary napkins, panty liners or incontinence protectors, may be used for the liquid-permeable sheet 4, and the aforesaid material is given solely by way of example.

The liquid-impermeable sheet 6 is comprised of a flexible material, preferably a thin plastic film of polyethylene (PE), polypropylene (PP) or a polyester, although it may be comprised of a laminate of a liquid-permeable material, such as nonwoven material, and a liquid-impermeable material. All materials used for the liquid impervious backing sheet of absorbent articles may be used.

The liquid-impermeable sheet is suitably provided with fastener means for fastening the article to a garment worn by the user, preferably to the inside of the wearer's panty in the crotch region thereof. Such fastener means may have the form of a pressure-sensitive binder, a touch-and-close tape, clamping means, a friction-enhancing coating, or a combination of two or more of these devices.

The absorbent layer 8 includes natural fibres, such as cellulose, cotton or peat fibres. Alternatively, absorbent synthetic fibres may be used, or a mixture of natural fibres and synthetic fibres. The absorbent layer 8 may also include a superabsorbent, i.e. a polymer that is capable of absorbing liquid in an amount corresponding to several times its own weight. The absorbent layer 8 may also include shape stabilising means and liquid dispersing means, and also a binding agent for holding together short fibres and particles to form a coherent unit. However, the absorbent layer shall be sufficiently flexible to enable it to be folded without breaking or damaging fibres to such an extent that would impair the liquid transporting properties of the layer as a result of folding the article.

A first end, the rear end 9, of the panty liner is intended to face towards the wearer's back, and a second end, the front end 10, is intended to face towards the wearer's stomach. The panty liner includes a central region 11 between the first and the second ends 9, 10.

When body fluid is delivered by the wearer of the panty liner, the liquid-permeable sheet 4 will allow the fluid to penetrate into the absorbent layer 8, meaning that the outer surface of the sheet 4 will remain dry and feel comfortable to the person wearing the panty liner. The body fluid is sucked up by the absorbent layer 8 and dispersed therein, such as to prevent reflux of the fluid back through the liquid-permeable sheet 4. The liquid-impermeable sheet 6 prevents wetting of the wearer's garment by the body fluid.

In a first embodiment of the invention, bellows-like pleats 12a, 12b extend in parallel relationship from the first end 9 to the central region 11 in a direction towards the second end 10. As will be evident from FIG. 2, the first pleat 12a has a cross-sectional shape in the form of a compressed Z (shown in a less compressed state in the Figure for the sake of clarity) and includes two vertically superimposed leg parts 14, 15 and an intermediate part 16 that extends between the leg parts 14, 15 and interconnects said parts. The second pleat 12b has a cross-sectional shape in the form of a mirror-image, compressed Z (shown in a less compressed state in the Figure for the sake of clarity) that includes leg parts 20, 21 and an intermediate part 22 which interconnects said leg parts. The upper leg parts 15 and 21 of respective bellow-like pleats 12a, 12b are directed towards each other and joined together by an interconnecting section 24.

The intermediate parts 16 and 22 are suitably releasably fastened to the upper leg parts 15, 21, so as to hold the pleats 12a, 12b together. In the illustrated embodiment, a continuous or discontinuous coating 26 of pressure-sensitive hot-melt glue is disposed on the liquid-impermeable sheet 6 of the intermediate part 16, 22. The legs parts 15, 21 and the interconnecting section 24, however, do not have a hotmelt coating. If a binder is also applied to the upper leg parts 15, 21, the binder on the intermediate parts 16, 22 and on the leg parts would stick together and cause problems when unfolding the pleats. It is, of course, also possible to provide a binder coating on the upper leg parts instead of on the intermediate parts. When a binder of lower adhesiveness is used, the binder may, of course, also be applied to the liquid-impermeable sheet 6 of both the upper leg parts and the intermediate parts. In the case of the illustrated embodiment, the binder coating 26 extends at least over parts of the liquid-impermeable sheet 6 in the regions where no pleats 12a, 12b are present, and forms a means for fastening the illustrated panty liner to the panties of a wearer. As previously mentioned, alternative fastener means, such as touch-and-close tapes, friction-enhancing coatings, clamping means or combinations of such devices may be used. Although the use of mechanical devices for releasably holding the pleats 12a, 12b together is conceivable, adhesive is preferred to this end regardless of the type of fastener means used to fasten the panty liner to the wearer's panties. Although not shown, the panty liner shown in FIGS. 1–3 includes a release paper or corresponding means for protecting the glue coating on the liquid-impermeable sheet 6 prior to using the panty liner.

When the bellows-like pleats 12a, 12b are drawn out or extended, the panty liner will obtain the generally rectangular shape shown in FIG. 3.

FIG. 4 is a schematic cross-sectional view, similar to that of FIG. 2, of a second embodiment of a panty liner 2', which includes three bellows-like pleats 12a' and three bellows-like pleats 12b'. It will be understood that the panty liner may include two pairs of pleats or more than three pairs of pleats.

FIG. 5 illustrates a third embodiment of the invention in which the pleats 12a", 12b" diverge from one another in a direction towards the central region 11".

In the illustrated embodiments, the intermediate parts of the pleats 12a, 12b; 12a', 12b' and 12a", 12b" have a constant width.

It will be understood that the described embodiments can be modified in several ways within the scope of the invention. The invention can be applied to absorbent articles other than panty liners, such as to sanitary napkins or incontinence protectors for instance, and the articles may have a shape other than rectangular when unfolded, e.g. an hourglass shape. The article may include any desired number of bellows-like pleats. Moreover, the absorbent body may be comprised of more than one layer of absorbent material. It is, of course, also conceivable to fold the rear part of the panty liner in a manner to increase or decrease the width of the bellows-like pleats in a direction towards the central region 11 and therewith obtain different shapes with regard to the rear part of the panty liner, instead of forming the pleats so that the intermediate parts have a constant width, as shown in the described embodiments. The invention is therefore limited solely by the contents of the accompanying Claims.

What is claimed is:

1. An absorbent article in the form of a sanitary napkin, a panty liner or an incontinence protector, comprising an elongated body that includes an expansion element for permitting the elongated body to expand in a direction generally transversely to the elongated body, wherein said elongated body is flat and has a liquid-permeable sheet that is adapted to face towards a wearer's body, a liquid-impermeable sheet that is adapted to face towards the wearer's garment, such as a pair of panties worn by the wearer, and an absorbent layer disposed between the liquid-permeable sheet and the liquid-impermeable sheet, and wherein at least part of the liquid-impermeable sheet includes a fastener for enabling the article to be releasably fastened to said garment, wherein said expansion element includes at least one pleat including said absorbent layer which pleat extends only partially along said elongated body and which Includes two leg parts disposed parallel with the plane of said article, and an Inwardly folded intermediate part which extends between the leg parts and joins said leg parts together.

2. The absorbent article according to claim 1, further comprising a second pleat, the two pleats forming a pair of mirror-imaged bellows disposed on respective sides of the longitudinal symmetry axis of the article, said pleats having a cross-sectional shape essentially in the form of a Z and a mirror-imaged Z respectively, wherein said leg parts, which lie in mutually the same plane, of the Z-shaped pleats in the pair of pleats face towards one another.

3. The absorbent article according to claim 2, that has a first end, a second end and a central region between said ends, wherein the pleats extend In the longitudinal direction of the article from the first end towards the second end and up to the central region.

4. The absorbent article according to claim 3, in which the pleats extend in mutually parallel relationship.

5. The absorbent article according to claim 3, in which the pleats are mutually divergent.

6. The absorbent article according to claim 1, in which the expansion element includes several pairs of pleats.

7. The absorbent article according to claim 1, in which the inwardly folded intermediate part or the leg parts is provided with a binder.

8. The absorbent article according to claim 7, in which at least part of the liquid-permeable sheet of the intermediate part or the leg parts is provided with a binder.

9. The absorbent article according to claim 1, in which the fastener is a binding agent.

10. The absorbent article according to claim 9, in which the binding agent is a pressure-sensitive hotmelt glue.

* * * * *